(12) United States Patent
Wong et al.

(10) Patent No.: US 6,894,049 B1
(45) Date of Patent: May 17, 2005

(54) PLATINUM COMPLEXES AS ANTITUMOR AGENTS

(75) Inventors: Ernest S. Y. Wong, Langley (CA); Christen M. Giandomenico, Blaine, WA (US)

(73) Assignee: AnorMED, Inc., Langley (CA)

(*) Notice: Subject to any disclaimer, the term of this patent is extended or adjusted under 35 U.S.C. 154(b) by 0 days.

(21) Appl. No.: 09/678,595

(22) Filed: Oct. 4, 2000

(51) Int. Cl.$^7$ .................. C07D 213/02; C07F 15/00; A61K 31/28; A61P 35/00

(52) U.S. Cl. ............... 514/252.1; 544/225; 514/365; 514/374; 514/378; 514/406; 548/146; 548/356.1; 548/215; 548/240

(58) Field of Search ............... 544/225; 514/252.1, 514/364, 374, 378, 406; 548/146, 356.1, 215, 240

(56) References Cited

U.S. PATENT DOCUMENTS

| | | | |
|---|---|---|---|
| 4,329,299 A | 5/1982 | Hydes | 260/429 |
| 4,533,502 A | 8/1985 | Rochon et al. | 546/8 |
| 4,760,155 A | 7/1988 | Heffernan et al. | 556/136 |
| 4,921,963 A * | 5/1990 | Skov et al. | 548/101 |
| 5,194,645 A | 3/1993 | Barnard | 556/137 |
| 5,244,919 A | 9/1993 | Abrams et al. | 514/492 |
| 5,547,982 A | 8/1996 | Abrams et al. | 514/492 |
| 5,624,919 A * | 4/1997 | Farrell | 514/184 |
| 5,665,771 A * | 9/1997 | Murrer | 514/492 |

FOREIGN PATENT DOCUMENTS

| | | |
|---|---|---|
| EP | 0287317 | 10/1988 |
| EP | 0727430 | 8/1996 |
| GB | 2137198 A | 10/1984 |
| WO | WO 95/07698 | 3/1995 |
| WO | WO 00/56743 | 9/2000 |
| WO | WO 00/61590 | 10/2000 |

OTHER PUBLICATIONS

CAS printout for Sok et al. Chem. Abstract 107: 129989 (1987).*
CAS printout for Muir et al. Chem. Abstract 108: 215259 (1988).*
CAS printout for Broomhead et al. Chem. Abstract 124: 248674 (1996).*
CAS printout for Wienkotter et al.*
CAS printout for Rochon et al.*
CAS printout for de Oliverira et al.*
Bierbach, U. et al.(1999) *Inorg Chem* 38(15):3535–3542.
Broomhead, J. et al. (1995) *Inorg Chim Acta* 240(1–2):13–17.
Matthews, J. et al. (1996) *Br J Cancer*, Suppl., 74(27):s200–s203.
Muir, M. et al. (1988) *Inorg Chim Acta* 151 (3):209–213.
Rochon, F. et al. (1991) *Inorg Chem* 30(24):4531–4535.
Saudek, V. et al. (1985) *J Inorg Biochem* 23(1):55–72.
Skov, K. et al. (1987) *Chem–Biol Interact* 62(2):117–129.
Skov, K. et al. (12987) *Radiat Res* 112(2):273–282.
Skov, K. et al. (1990) *Int J Radiat Biol* 57(5):947–958.
Holford et al., Anti–Cancer Drug Des. (1998) 13:1.
Holford et al., Br. J. Cancer (1998) 77:366.
Kelland et al., Cancer Res. (1992) 52:822.
Kelland et al., Cancer Res. (1992) 52:3857.
Kelland et al., Cancer REs. (1993) 53:2581.
Raynaud et al., Clin. Cancer Res. (1997) 3:2063–2074.
Wong et al., Chem. Rev. (1999) 9:2451–2466.
Abrams et al., Inorg. Chim. Acta (1987) 131:3–4.
Braddock et al., Chem. Biol. Interactions (1975) 11:145–161.
Courtot et al., J. Organometallic Chem. (1978) 145:343–357.
Giandomenico et al., Inorg. Chem. (1995) 34:1015–1021.
Holford et al., Anti–Cancer Drug Des. (1998) 13:1.
Holford et al., Br. J. Cancer (1998) 77:366–373.
Kelland et al., Cancer Res. (1992) 52:822.
Kelland et al., Cancer Res. (1992) 52:3857.
Kelland et al., Cancer Res. (1992) 53:2581.
Kong and Rochon, Canadian J. Chem. (1978) 56:441–445.
Kong, P.–C. et al. (1978), "Reactions of Potassium Tetrachloroplatinate (11) with Pyridine Derivatives in Dimethylformamide and Synthesis of Potassium Trichloro(pyridine-)platinum(11)," *Chemical Abstracts* 89(4): abstract No. 35686.

(Continued)

*Primary Examiner*—John M. Ford
*Assistant Examiner*—Hong Liu
(74) *Attorney, Agent, or Firm*—Morrison & Foerster, LLP

(57) ABSTRACT

The present invention relates to platinum antitumor drugs. In particular, it relates to platinum complexes having formula Ia or Ib

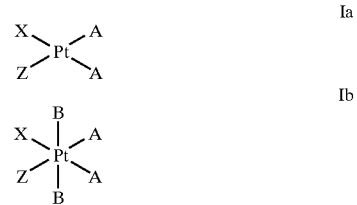

or a pharmaceutically acceptable salt thereof
wherein:
each A is independently an anion;
each B is independently halo, hydroxy, carboxylate, carbamate or a carbonate ester,
Z is a substituted 5- or 6-membered, heterocyclic moiety wherein at least one substituent sterically hinders access of the Pt atom to a DNA strand of a tumor cell, and wherein Z is other than pyridine; and
X is $NH_3$ or mono- or dialkyl substituted $NH_3$.
which are active against cancer cells and have improved aqueous solubility and activity.

15 Claims, No Drawings

OTHER PUBLICATIONS

Kong et al., Can. J. Chem. (1979) 57:682–684.
Raynaud et al., Clin. Cancer Res. (1997) 3:2063–2074.
Rochon, F.D. et al. (1988). "Synthesis and Studies of Platinum (II) Compounds of the Types K'Pt(amine)C13! and 'Pt(amine)(acetonitrile)C12!," *Chemical Abstracts* 108(24): abstract No.215224.
Rochon, F.D. et al., Can J. Chem., 64:1894–1896 (1986).
Rochon, F.D. et al., Can J. Chem., 74:2121–2130 (1996).
Rochon, F.D. et al., Can J. Chem., 58: 97–101 (1980).
Rochon, F.D. et al., Can J. Chem., 33:4485–4493 (1994).
Talman et al., Chemical Abstracts (1997) 126(4):abstract No. 194433.
Wong et al., Chem. Rev. (1999) 9:2451–2466.

* cited by examiner

(12) United States Patent

PLATINUM COMPLEXES AS ANTITUMOR AGENTS

TECHNICAL FIELD

The present invention relates to the area of platinum antitumor drugs which are active against cancer cells and have improved aqueous solubility and activity.

BACKGROUND ART

Interest in platinum-based antitumor drugs has its origin in the discovery of the inhibitory effects of platinum complexes on cell division. Subsequent research and development led to the approval of the use of cisplatin, $[PtCl_2(NH_3)_2]$ for cancer therapy. Cisplatin is now widely accepted and is one of the three most widely utilized antitumor drugs in the world. However, cisplatin has several disadvantages that include severe toxicity such as nephrotoxicity, neurotoxicity and emetogenesis. Cisplatin also has limited aqueous solubility (1 mg/ml) and is effective in a narrow range of tumors. Some tumors have natural resistance to platinum drugs while others develop resistance after the initial treatment.

In addition to cisplatin, carboplatin or diammine[1,1-cyclobutanedicarboxylato (2-)]-O,O'-platinum(II) has also received worldwide approval for use in cancer therapy. Carboplatin is less toxic than cisplatin and has greater aqueous solubility (14 mg/ml) but it is still only active in the same range of tumors as cisplatin. Many platinum complexes have been studied in an attempt to overcome the limitation of cisplatin (Wong, E.; et al., *Chem. Rev.* 1999, 9, 2451–2466).

A class of platinum compounds that has been reported to have activity against cancer is mixed amine platinum complexes of the general formula $Pt(L)(L')A_2$ or $Pt(L)(L')A_2B_2$ where L and L' are different amines, and where one of the amines sterically hinders access of Pt to the DNA of the tumor cell. One example within this class of compounds is cis-ammine(2-methylpyridine)dichloroplatinum(II) (Holford, J. F.; et al., *Anti-Cancer Drug Des.* 1998, 13, 1 and Raynaud, F. I., et al., *Clin. Cancer Res.* 1997, 3, 2063–2074 and Holford, J. F., et al., *Br. J. Cancer* 1998, 77, 366 and U.S. Pat. No. 5,665,771). Other examples of antitumor compounds are bis-acetato-ammine(cyclohexylamine) dichloroplatinum(IV) and bis-butyrato-ammine (cyclohexylamine)dichloroplatinum(IV) (Kelland, L. R.; et al., *Cancer Res.* 1992, 52, 3857; Kelland, L. R., et al., *Cancer Res.* 1992, 52, 822; Kelland, L. R.; et al., *Cancer Res.* 1993,53, 2581 and U.S. Pat. No. 5,244,919.

The mixed amine platinum compounds have been reported to have antitumor activity in cisplatin resistant tumors. To compare the ability of various compounds to overcome platinum drug resistance, resistance factors are calculated for sets of cell lines. The resistance factor is defined as the ratio:

$$\frac{\text{activity against a parent line of cancer cells}}{\text{activity against a derivative of that cell line that has developed resistance to cisplatin}}$$

Thus, small resistance factors are preferred since the compound is better able to overcome the drug resistance of the cancer cells. The above cited compounds, Cis-ammine (2-methylpyridine)dichloroplatinum(II), bis-acetatoammine (cyclohexylamine)dichloroplatinum(IV) and bis-butyratoammine-(cyclohexylamine)dichloroplatinum(IV) were reported to have activity in certain cisplatin resistant tumors, but do not have equivalent activity in all cancer cells with different mechanisms of platinum drug resistance. For example, bis-acetato-ammine(cyclohexylamine) dichloroplatinum(IV) and bis-butyrato-ammine (cyclohexylamine)dichloroplatinum(IV) have lower resistance factors in the set of 41 M/41 MR cancer cell lines than in the A2780/A2780R or CH1/CH1R sets of cells. On the other hand, cis-ammine(2-methylpyridine)dichloroplatinum (II) has a higher resistance factor in A2780/A2780R cell lines than in the 41M/41MR and CH1/CH1R cell lines. The platinum drug resistance in 41 MR cells is due to reduced platinum accumulation, while in CH1R cells, the resistance is due to enhanced removal of and/or increased tolerance to Pt-DNA adducts. Resistance in A2780R cancer cells is due to detoxification via elevated glutathione levels, decreased uptake and increased DNA repair.

Despite the improved activity of these mixed amine platinum compounds compared to cisplatin in some platinum drug resistant cancer cells, their solubility in aqueous solution is limited; their aqueous solubility at ambient temperature and neutral pH are even lower than that of cisplatin. The limited aqueous solubility poses difficulties in the formulation and administration of these compounds. In particular, the iv administration of a platinum drug with low aqueous solubility may require the infusion of a large volume of liquid in order to achieve the therapeutic dose; a potentially long and inconvenient process.

Increasing the water solubility of platinum antitumor compounds has been an important practical objective of many platinum drug development programs. The solubility of cisplatin (~1 mg/ml) approaches the practical limit of solubility for a cytoxic agent of its potency that is administered parenterally. Orally administered compounds can be less soluble, but they must be soluble enough to be absorbed. There is a desire to design platinum drugs with improved aqueous solubility as well as improved antitumor activity, particularly in cisplatin resistant tumors.

U.S. Pat. No. 5,665,771 describes and claims a genus which contains the compounds of the present invention. The invention compounds, however, are not specifically taught or suggested in the above-referenced patent, and have improved solubility and/or antitumor activity characteristics as compared to the compounds exemplified in the '771 patent.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

DISCLOSURE OF THE INVENTION

The present invention provides cis-platinum complexes having formula Ia or Ib

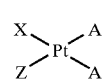

Ia

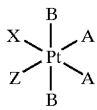

and their pharmaceutically acceptable salts
wherein:
A are anions which are the same or different, which are suitably halo, especially chloro, hydroxy, carboxylate, carbamate, carbonate ester or together form a bi-dentate carboxylate or sulfate,
B are the same or different and are halo, hydroxy, carboxylate, carbamate or carbonate ester,
Z is a 5- or 6-membered substituted heterocyclic moiety wherein at least one substituent sterically hinders access of the Pt atom to a DNA strand of a tumor cell and wherein said heterocyclic moiety is other than pyridine; and
X is $NH_3$ or mono- or dialkyl substituted $NH_3$, These complexes are active against cancer cells and have improved aqueous solubility and activity.

Thus, according to a further aspect of the invention, there is provided a complex of formula Ia or Ib for use in medicine and in particular for use in the treatment of cancer. A still further aspect of the invention provides the use of a complex of formula Ia or Ib in the manufacture of a medicament for the treatment of cancer. The invention is directed to a method of treating cancer comprising administering to a subject in need thereof, a pharmaceutically effective amount of a complex of formula Ia or Ib.

MODES OF CARRYING OUT THE INVENTION

The present invention provides compounds which have enhanced properties in terms of solubility and antitumor activity. The compounds of the invention form a subset of those described in U.S. Pat. No. 5,665,771. In general, while compounds of formula Ia may comprise, as Z, a 5 or 6 member heterocycle, preferably they comprise as Z a 5-membered heterocyclic substituent. Those of formula Ib may also comprise, as Z, a 5 or 6 member heterocycle, but preferably they comprise a 6-membered pyrazine, pyrimidine, or pyridazine substituent or a substituted imidazole. In all cases, these heterocyclics are substituted by at least one substituent so that access of the platinum ion to the DNA in tumor cells is sterically hindered. Preferably, this substituent is at a position adjacent to the coordinating heteroatom.

In both formulas Ia and Ib, anions represented by A selected from those known to those skilled in the art. The appropriate anions may be halo, carboxylate, carbamate, carbonate esters, hydroxy, or may together form a dicarboxylate or sulfate. Preferably, both A are halo, preferably chloro.

In compounds of formula Ib, each B is an anion and is independently halo, hydroxy, carboxy, carbamate or carbonate ester. Preferably, B is hydroxy or a carboxylate; more preferably, both of the B substituents are the same.

When the complex is of formula Ia, Z is a preferably 5-membered substituted heterocyclic moiety. Although Z may be pyrazine, Z is preferably imidazole, pyrazole, pyrrole, oxazole, isoxazole, thiazole, furan, thiophene, thiadiazole or thiatriazole. More preferred embodiments of Z are imidazole, pyrazole, oxazole, isoxazole, thiazole and pyrazine. It is also preferred that Z is coordinated to the platinum atom through a nitrogen atom, though coordination via an oxygen or sulfur atom is also envisioned.

Substituents on the heterocycle are preferably alkyl of 1 to 4 carbon atoms, particularly methyl. It is preferred that at least one substituent be at a position on the heterocycle adjacent to the coordinating atom. However, compounds wherein a substituent is present one atom removed from the coordination atom wherein sufficient steric hindrance is provided are also included within the scope of the invention.

In the compounds of formula Ib, Z is preferably a 6-membered heterocyclic moiety, most preferably a pyridazine, a pyrimidine, or a pyrazine moiety. In other preferred embodiments of formula Ib, Z is an imidazole, substituted by lower alkyl (1–4 C). It is also preferred that at least one substituent reside at an atom adjacent to the coordinating nitrogen atom, but again, compounds comprising only more distant substituents which supply sufficient steric hindrance are also included within the scope of the invention.

It is noted in the above description that the essential feature of the substituent at Z is that it provides steric hindrance to access of the platinum atom to a DNA strand of a tumor cell. As stated above, this may readily be achieved by the presence of at least one substituent on an atom of the heterocycle which is adjacent to the coordinating atom on the ring. However, an additional group of compounds within the scope of the invention is typified by those of Examples 3 and 12 where the presence of a substituent more distant from the coordinating atom nevertheless results in sufficient steric hindrance. Thus, in another aspect, the invention is directed to compounds of formulas Ia or Ib wherein the substituent on the heterocycle is at a position other than the position adjacent to the coordinating atom.

The complexes of formula Ia and Ib may be prepared by methods known in the art. General preparation of platinum complexes with mixed ammine/alkylamine ligands are given by Braddock, P. D., et al., Chem.-Biol. Interactions 1975, 11, 145–161; and Giandomenico, C. M., et al., Inorg. Chem. 1995, 34, 1015–1021.

For complexes of formula Ia where X is $NH_3$ and A is chloride, a common synthetic method is to react $[PtCl_3(NH_3)]^-$ with Z to produce the desired complex. $[PtCl_3(NH_3)]^-$ can be prepared from $[PtCl_4]^{2-}$ using methods known in the art (Giandomenico, C. M., Inorg. Chem. 1995, supra, and Abrams, J. J., et al., Inorg. Chim. Acta 1987 131, 3–4). Another synthetic method is to prepare $[PtCl_3(Z)]^-$ from $[PtCl_4]^{2-}$ starting material and then react with $NH_3$ or other substituted $NH_3$ to produce the desired complex.

The complexes of this invention have equivalent or greater aqueous solubility as compared to cisplatin, cis-ammine(2-methylpyridine)dichloroplatinum(II), bis-acetato-ammine(cyclohexylamine)dichloroplatinum(IV) and bis-butyrato-ammine(cyclohexylamine)dichloroplatinum(IV). For platinum(II) compounds of formula Ia, there is a 1.3 to 12 fold increase in aqueous solubility compared to cisplatin and cis-ammine(2-methylpyridine)dichloroplatinum(II). For the platinum(IV) compounds of formula Ib, there is a 2.6 to 100 fold increase in solubility compared to cisplatin, bis-acetato-ammine (cyclohexylamine)dichloroplatinum(IV) and bis-butyrato-ammine(cyclohexylamine)dichloroplatinum(IV). In general, the greater aqueous solubility of the complexes allows for an easier formulation and administration of the drug. This is particularly important for intravenous administration; a higher aqueous solubility would allow for a higher drug dose to be intravenously administered in a smaller volume of saline.

The complexes of the invention demonstrate activity against cancer cells, particularly against cancer cells resistant to cisplatin and carboplatin. In particular, the complexes of the invention exhibit reduced resistance factors compared to cisplatin and carboplatin. As stated above, resistance factor is defined as the ratio of the activity of a complex against a parent line of cancer cells to the activity against a derivative of that cell line that has developed resistance to cisplatin. The lower the resistance factor, the greater the ability of the drug to overcome the platinum drug resistance in that cancer cell line. A resistance factor of one would be ideal. The resistance factors for cisplatin in A2780/A2780R, CH1/CH1R and 41M/41MR sets of cancer cell lines are about 16, 7 and 5, respectively. It is not, of course, surprising that the resistance factors for cisplatin itself are fairly high, but the other commercial complex, carboplatin, is also less effective with cisplatin resistant cell lines. The resistance factor for carboplatin in A2780/A2780R, CH1/CH1R and 41M/41MR sets of cancer cell lines are about 15, 5 and 3, respectively. For complexes of the invention, the resistance factors in CH1/CH1R and 41M/41MR sets of cancer cell lines are approximately 2, a 2 to 7 fold decrease compared to cisplatin. In A2780/A2780R cancer cell lines, the resistance factors for complexes of the invention ranged from 1.8 to 8, a 2 to 9 fold decrease compared to cisplatin and carboplatin. In particular, for [PtCl$_2$(NH$_3$)(1,3,5-trimethylpyrazole)], the resistance factor for A2780/A2780R cells was 1.8, an 8 to 9 fold decrease compared to cisplatin and carboplatin.

The complexes of the invention also exhibited comparable and, in some cancer cells, lower resistance factors than cis-ammine(2-methylpyridine)dichloroplatinum(II), bis-acetato-ammine(cyclohexylamine)dichloroplatinum(IV) and bis-butyrato-ammine(cyclohexylamine)dichloroplatinum(IV). For complexes of formula Ia with Z being 5-membered heterocyclic compounds with more than one heteroatom, the resistance factors were, unexpectedly, comparable to that of cis-ammine(2-methylpyridine)dichloroplatinum(II). In particular, complexes of formula Ia where Z is a 5-membered heterocyclic ring with more than one nitrogen heteroatom surprisingly exhibit even lower resistance factors than cis-ammine(2-methylpyridine)dichloroplatinum(II) in A2780/A2780R cancer cell lines. More specifically, the complex, [PtCl$_2$(NH$_3$)(1,3,5-trimethylpyrazole)] exhibited a 2.6 fold decrease in resistance factor for the A2780/A2780R cell lines compared to cis-ammine(2-methylpyridine)dichloro-platinum(II). It was also surprising to observe that [PtCl$_2$(NH$_3$)(1,3,5-trimethylpyrazole)] appears to be less toxic than cisplatin and than cis-ammine(2-methylpyridine)dichloro-platinum (II). The maximum tolerated dose (MTD) in mice for [PtCl$_2$(NH$_3$)(1,3,5-trimethylpyrazole)] was greater than 50 mg/Kg. This is greater than the MTD of either cisplatin or cis-ammine(2-methylpyridine)dichloroplatinum(II) which doses are 11.3 mg/Kg and 40 mg/Kg, respectively. Thus, the complexes exemplified herein expand the repertoire of available spectra of characteristics available for pharmaceutical use.

The active complexes may be administered in the form of pharmaceutical compositions formulated according to well-known principles. Thus a still further aspect of the present invention provides a pharmaceutical composition comprising a compound of formula Ia or Ib or their salts in admixture with a pharmaceutically acceptable diluent or carrier and optionally one or more other therapeutic agents. Suitable salts may include anionic salts such as chlorides, sulfates and the like, or may be salts of organic anions such as acetates. Inorganic salts are preferred. The pharmaceutical compositions may be in the form of solutions of suspensions for injection, or to be in capsule, tablet, dragee, or other solid composition or as a solution or suspension for oral administration or formulated into pessaries or suppositories, or sustained release form of any of the above. Suitable diluents, carriers, excipients and other components are known. It may be desirable also to formulate a composition for topical administration such as an ointment or cream, or to be administered as a transdermal patch. Suitable formulations appropriate for any route of administration are known in the art and will be found, for example, in *Remington's Pharmaceutical Sciences*, latest ed., Mack Publishing Co., Easton, Pa.

The pharmaceutical compositions according to the invention may contain dosages determined in accordance with conventional pharmaceutical methods, suitably to provide active compounds in the dosage range in humans of from 0.1 to 100 mg/Kg body weight per day, in a single unit dose of in a number of smaller unit doses. Preferred dosage ranges are 1 to 30 mg/Kg body weight per day.

It will be understood, of course, that an individual dose appropriate for a particular subject is variable depending on the severity of the condition of the subject, the route of administration, the formulation, and the judgment of the attending practitioner. The dosages given above are typical, and it may be appropriate in some instances to provide dosages that are outside the ranges specified.

The complexes of the invention may be administered alone or in combination with another chemotherapeutic agents such as gemcitabine, etoposide or taxol, either as a single treatment or course of treatment or as part of combined therapy with other pharmaceuticals to overcome or diminish side effects or to improve bioavailability, or in combination with other therapies such as radiation treatment.

The following examples are provided for illustration, and are not intended to be limiting of the present invention.

EXAMPLES

Example 1

(SP-4-3)-amminedichloro(3.5-dimethylpyrazole) platinum(II)

K[PtCl$_3$(NH$_3$)] (2.10 g, 5.89 mmol) was dissolved in 15 ml of 0.25 N KCl. KI (2.94 g, 17.7 mmol) was dissolved in 2 ml of 0.25 N KCl and 3,5-dimethylpyrazole (0.63 g, 6.55 mmol) was dissolved in 2 ml of 0.25 N KCl. The KI solution was added to the K[PtCl$_3$(NH$_3$)] solution, followed by the 3,5-dimethylpyrazole solution. The combined solution was stirred in the dark for 2–3 h at ambient temperature. Yellowish orange precipitate formed. The precipitate was collected, washed with water and then methanol, and dried under vacuum at ambient temperature overnight. The mass of the isolated precipitate was 2.76 g and was confirmed by Pt-195 NMR to be [Pt(I)Cl(NH$_3$)(3,5-dimethylpyrazole)]. The be [Pt(I)Cl(NH$_3$)(3,5-dimethylpyrazole)] was placed in 10 ml of water and 3–4 ml of acetone. Silver nitrate (1.51 g, 8.88 mmol) was added to the suspension. It was then stirred for 24 h in the dark at ambient temperature. The suspension was filtered and 2–3 ml of concentrated HCl (~12 M) was added to the filtrate. The solution was stirred at ambient temperature for 3–4 h, during which time, pale yellow precipitate formed. The precipitate was washed with water and then acetone and was dried under vacuum at ambient temperature for 24 h and weighed. Yield: 0.46 g (21%). Anal. Calcd (found) for $C_5H_{11}N_3Cl_2Pt$: C, 15.84 (15.94); H, 2.92 (2.90); N, 11.08 (11.03); Cl, 18.08 (18.79).

Example 2

(SP-4-3)-amminedichloro(1,3,5-trimethylpyrazole) platinum(II)

$K[PtCl_3(NH_3)]$ (2.03 g, 5.69 mmol) was dissolved in 15 ml of 0.25 N KCl. KI (2.84 g, 17.1 mmol) was dissolved in 2 ml of 0.25 N KCl and 1,3,5-trimethylpyrazole (0.71 g, 6.44 mmol) was dissolved in 2 ml of 0.25 N KCl. The KI solution was added to the $K[PtCl_3(NH_3)]$ solution, followed by the 1,3,5-trimethylpyrazole solution. The combined solution was stirred in the dark for 2–3 h at ambient temperature. Yellowish orange precipitate formed. The precipitate was collected, washed with water and then methanol, and dried under vacuum at ambient temperature overnight. The precipitate was confirmed by Pt-195 NMR to be $[Pt(I)Cl(NH_3)(1,3,5\text{-trimethylpyrazole})]$. The $[Pt(I)Cl(NH_3)(3,5\text{-dimethylpyrazole})]$ was placed in 10 ml of water and 3–4 ml of acetone. Silver nitrate (1.23 g, 7.24 mmol) was added to the suspension. It was then stirred for 24 h in the dark at ambient temperature. The suspension was filtered and 2–3 ml of concentrated HCl (~12 M) was added to the filtrate. The solution was stirred at ambient temperature for 3–4 h, during which time, pale yellow precipitate formed. The precipitate was washed with water and then acetone and was dried under vacuum at ambient temperature for 24 h and weighed. Yield: 1.21 g (54%). Anal. Calcd (found) for $C_6H_{13}N_3Cl_2Pt$: C, 18.43 (18.45); H, 3.35 (3.45); N, 10.72 (10.65); Cl, 17.99 (17.96).

Examples 3–10

Additional Compounds

A. Using analogous procedures, the following compounds were prepared:

dimethylpyrazine was mixed with 1 ml of NMP. Approximately four equal portions of the 2,5-dimethylpyrazine solution were added to the reaction mixture in 30 minute intervals. After the last addition, the reaction was allowed to proceed for 60 minutes and was then cooled to ambient temperature. 150 ml of methylene chloride was added to the reaction mixture. The addition of methylene chloride caused the precipitation of the product. The precipitate was collected by vacuum filtration using a glass frit and was washed with methylene chloride (3×30 ml) and diethyl ether (3×10 ml). The precipitate was dried under vacuum at ambient temperature for 16 hours and weighed. Yield: 1.0507 g (66.3%). Anal. Calcd (found) for $C_6H_8N_2Cl_3KPt.2.2KCl$: C, 11.73 (11.50); H, 1.31 (1.50); N, 4.56 (4.27); Cl, 30.14 (29.86). $^1H$ NMR (300 MHz, DMF-$d^7$) 9.11 (s, 1 pyrazine H); 8.68 (s, 1 pyrazine H); 3.31 (s, 3 methyl H), 2.68 (s, 3 methyl H).

0.5325 g (0.8665 mmoles) of $K[PtCl_3(2,5\text{-dimethylpyrazine})].2.2$ KCl was charged to a 15 ml round bottom flask and 1.0 ml of 2.5 M KCl solution added. 0.335 g (4.35 mmoles) of ammonium acetate was dissolved in 1.75 ml of 2.5 M (4.38 mmoles) ammonium hydroxide solution and added to the stirring reaction mixture. The reaction mixture was immersed in a 45° C. oil bath. After 15 minutes, the mixture became yellow in colour. After 1 hour, the mixture was cooled to ambient temperature and the yellow precipitate collected by vacuum filtration using a glass frit. The precipitate was washed with water (2×10 ml) and acetone (1×10 ml) and dried under vacuum at ambient temperature. $^1H$ NMR (300 MHz, DMF-$d^7$): 9.16 (s, 1 pyrazine H); 8.80 (s, 1 pyrazine H); 4.70 (bs, 3 $NH_3$ H), 3.26 (s, 3 methyl H); 2.69 (2, 3 methyl H).

Example 11

(OC-6-43)amminedichlorodihydroxo-(3.5-dimethylpyrazole)platinum(IV)

1.0 ml of water and 1.0 ml 30% $H_2O_2$ was added to a suspension of 1.0064 g of cis-$[PtCl_2(NH_3)(3,5$-

|  |  |  |  | Microanalysis % Calculated (Found) | | | |
|---|---|---|---|---|---|---|---|
| Example | Z | A | Yield | C | H | N | Cl |
| 3 | 1-methylimidazole | Cl | 79% | 13.16 (13.28) | 2.48 (2.52) | 11.51 (11.42) | 19.42 (19.50) |
| 4 | 3,5-dimethylisoxazole | Cl | 64% | 15.80 (15.89) | 2.65 (2.62) | 7.37 (7.29) | 18.65 (18.54) |
| 5 | 2,5-dimethylpyrazine | Cl | 88% | 18.42 (18.56) | 2.83 (2.93) | 10.74 (10.74) | 18.12 (18.13) |
| 6 | 2,3-dimethylpyrazine | Cl | 86% | 18.42 (18.49) | 2.83 (2.87) | 10.74 (10.65) | 18.12 (18.25) |
| 7 | 1,2-dimethylimidazole | Cl | 45% | 15.84 (15.89) | 2.92 (2.94) | 11.08 (10.90) | 18.70 (18.60) |
| 8 | 2-methylimidazole | Cl | 15% | 9.74 (9.75) | 1.84 (1.85) | 9.46 (9.40) | 23.51 (23.49) |
| 9 | 2,5-dimethylimidazole | Cl | 45% | 15.57 (15.40) | 1.68 (1.72) | 2.59 (2.60) | 27.83 (27.70) |
| 10 | 2,4,5-trimethyloxazole | Cl | 40% | 18.28 (18.40) | 3.07 (3.04) | 7.11 (7.05) | 17.99 (17.85) |

B. Alternative synthesis of example 5, $K[PtCl_2(NH_3)(2,5$-dimethylpyrazine)](Example 5)

$K_2PtCl_4$ was ground to a very fine powder with a mortar and pestle. 1.0724 g (2.58 mmoles) of $K_2PtCl_4$ was charged to a 10 ml round bottom flask and ~5 ml of NMP added. The reaction vessel was stirred at ~700 rpm and immersed in an oil bath at 65° C. 0.3196 g (2.96 mmoles) of 2,5- dimethylpyrazole)] in 10 ml of heptane. This mixture was stirred and heated to ~80° C. for 2.5 hours. The mixture was cooled to room temperature and then stirred for 1 hour in an ice bath. The bright yellow solid was collected by vacuum filtration and washed with water and methanol. The product was dried under vacuum at ambient temperature overnight. Yield: 0.7797 g (71%). Anal. Calcd (found) for $C_5H_{13}N_3Cl_2O_2Pt$: C, 14.54 (14.75); H, 3.17 (3.27); N, 10.17 (10.16); Cl, 17.16 (17.09).

Example 12

(OC-6-43)-amminedichlorodihydroxo-(1-methylimidazole)platinum(IV)

1.5 ml of water and 1.5 ml 30% $H_2O_2$ was added to a suspension of 0.9291 g of cis-$[PtCl_2(NH_3)(1$-methylimidazole)] in 7 ml of heptane. This mixture was stirred and heated to ~80° C. for 2.5 hours. The solution was lyophilized to yield a bright yellow solid. Yield: 0.4 g (39%). Anal. Calcd (found) for $C_4H_{11}N_3Cl_2O_2Pt$: C, 12.04 (12.12); H, 2.78 (2.85); N, 10.53 (10.54); Cl, 17.76 (17.66).

Example 13

(OC-6-43)-ammninedichlorodihydroxo-(2.3dimethypyrazine)platinum(IV)

2.5 ml of water and 3.5 ml 30% $H_2O_2$ was added to a suspension of 1.6731 g of cis-$[PtCl_2(NH_3)(2,3$-dimethylpyrazine)] in 10 ml of heptane. This mixture was stirred and heated to ~80° C. for 2 hours. The mixture was cooled to room temperature and then stirred for 1 hour in an ice bath. The bright yellow solid was cooled by vacuum filtration and washed with water and methanol. The product was dried under vacuum at ambient temperature overnight. Yield: 1.1341 g (62%). Anal. Calcd (found) for $C_6H_{13}N_3Cl_2O_2Pt$: C, 16.95 (16.81); H, 3.08 (3.12); N, 9.88 (9.66); Cl, 16.68 (16.44).

Example 14

(OC-6-43)-amminedichlorodiacetato-(2,3-dimethylpyrazine)platinum(IV)

c,t,c-$[PtCl_2(OH)_2(NH_3)(2,3$-dimethylpyrazine)] was added in small portions to of acetic anhydride at 0° C. This mixture was stirred vigorously at room temperature. After 4 days, the solid was collected by vacuum filtration and washed with diethyl ether. The product was dried under vacuum at ambient temperature overnight. Yield: g (%). Anal. Calcd (found) for $C_{10}H_{17}N_3Cl_2O_4Pt$: C, 23.59 (23.51); H, 3.36 (3.38); N, 8.25 (8.21); Cl, 13.92 (13.81).

Examples 15–16

Additional Compounds

Using analogous procedures, the following compounds were prepared:

Example 17

Solubility Analysis

The aqueous solubility of platinum complexes of the invention at ambient conditions is as shown in Table 1.

TABLE 1

| Compounds | Aqueous Solubility |
|---|---|
| cisplatin | 1 mg/ml |
| cis-ammine(2-methylpyridine)dichloroplatinum(II) | 0.7 mg/ml |
| bis-butyrato-ammine-(cyclohexylamine)dichloro platinum(IV) | 0.2 mg/ml |
| bis-acetato-ammine-(cyclohexylamine)dichloro platinum(IV) | <1 mg/ml |
| Example 1 | 11.6 mg/ml |
| Example 2 | 7.2 mg/ml |
| Example 3 | 4.3 mg/ml |
| Example 4 | 1.27 mg/ml |
| Example 5 | 0.8 mg/ml |
| Example 6 | 0.8 mg/ml |
| Example 7 | 2.1 mg/ml |
| Example 8 | 9 mg/ml |
| Example 9 | 6.2 mg/ml |
| Example 10 | 5.4 mg/ml |
| Example 11 | 2.6 mg/ml |
| Example 12 | >1000 mg/ml |
| Example 14 | 7 mg/ml |
| Example 15 | 9 mg/ml |
| Example 16 | 7.35 mg/ml |

As shown in Table 1, the compounds of Examples 1–3 and 7–16 have substantially higher solubility than cisplatin, and as compared to the additional prior art compounds set forth. The compound of Example 12 shows exceptional solubility.

Example 18

Determination of Resistance Factor

The complexes of the invention were tested against human cancer cell lines grown in cell culture according to established testing procedures (described by Holford, et al., *British J. Cancer* 1998 77(3) 366–373). The results are shown below in Table 2. The results are given in concentrations ($\mu$M) necessary to achieve a 50% decrease in cell proliferation, with resistance factors in brackets for the cisplatin-resistant cell lines. The cell lines bred to be resistant to cisplatin have the designation R, as in 41MR.

| | | | Microanalysis % Calculated (Found) | | | | |
|---|---|---|---|---|---|---|---|
| Example | Z | A | B | C | H | N | Cl |
| 15 | 1,2-dimethylimidazole | Cl | OH | 13.89 | 3.53 | 9.73 | 16.39 |
| | | | | (12.96) | (3.49) | (9.62) | (16.37) |
| 16 | 2,5-dimethylimidazole | Cl | OH | 13.85 | 3.55 | 9.69 | 16.35 |
| | | | | (13.97) | (3.53) | (9.64) | (16.26) |

TABLE 2

| Compounds | 41M | 41MR | CH1 | CH1R | A2780 | A2780R |
|---|---|---|---|---|---|---|
| cisplatin | 0.26 | 1.2(4.6) | 0.11 | 0.71(6.5) | 0.33 | 5.2(15.7) |
| carboplatin | 3.3 | 8.8(2.7) | 1.3 | 6(4.5) | 1.8 | 25.9(14.4) |
| cis-ammine(2-methylpyridine)dichloro platinum(II) | 5.6 | 6(1.1) | 2.2 | 2.1(1) | 2.5 | 12(4.8) |
| bis-acetato-ammine-(cyclohexylamine)dichloro platinum(IV) | 0.5 | 0.6(1.2) | 1.0 | 0.4(4) | 0.4 | 1.84(4.6) |
| bis-butyrato-ammine-(cyclohexylamine)dichloro platinum(IV) | 0.072 | 0.048(0.67) | 0.0066 | 0.024(3.7) | NA | NA |
| Example 1 | 3.5 | 4.5(1.3) | 2.05 | 3.8(1.9) | 2.7 | 9.2(3.4) |
| Example 2 | 8.5 | 15.5(1.8) | 9.2 | 11(1.2) | 8.5 | 15.5(1.8) |
| Example 3 | 7.4 | 12.5(1.7) | 7.6 | 10.5(1.4) | 6.4 | 16.5(2.6) |
| Example 4 | 8 | 6(0.8) | 3.2 | 8(2.5) | 3.7 | 23.5(6.4) |
| Example 5 | 11.5 | 9(0.8) | 5 | 8(1.6) | 6 | 35(5.8) |
| Example 6 | 6.6 | 6.5(1.0) | 3.2 | 5.4(1.7) | 3.4 | 17.5(5.1) |
| Example 7 | 9.3 | 15(1.6) | 8.3 | 12(1.4) | 7.1 | 17.5(2.5) |
| Example 8 | 21 | 16.5(0.8) | 5.2 | 12.5(2.5) | NA | NA |
| Example 9 | 9.3 | 15(1.6) | 8.8 | 13(1.5) | 13.5 | 39.5(2.9) |
| Example 10 | 11.8 | 11.5(1.0) | 5.2 | 9.4(1.8) | 9.8 | 40(4.1) |
| Example 11 | 11 | 8.2(0.7) | 2 | 5(2.5) | 7.2 | 37(5.1) |
| Example 12 | 23.5 | 45(1.9) | 13 | 24.5(1.9) | 17 | 77(4.5) |
| Example 14 | 29 | 36(1.2) | 9.4 | 30(3.2) | NA | NA |
| Example 15 | 23 | 21(0.9) | 12 | 16.5(1.4) | 13.5 | >100(>7.4) |
| Example 16 | 19 | 28(1.5) | 10 | 21(2.1) | 12.5 | >100(>8) |

As shown in Table 2, the activity of the compounds of the invention in inhibiting resistant cell lines is comparable to that of the prior art compounds, at least in some cell lines. The resistance factors with respect to 41 M/41MR are particularly favorable with respect to the compounds of Examples 4–6 and 10–11. This enhanced activity mitigates the relatively low solubility of the compounds of Examples 5–6, although the solubility is comparable, still, to that of cisplatin and is more favorable than that of the remaining prior art compounds.

Thus, taken together, the invention compounds represent improved characteristics over those of the prior art.

We claim:

1. A cis-platinum complex of the formula Ia or Ib

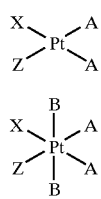

or a pharmaceutically acceptable salt thereof
wherein:
each A is independently halo, hydroxy or carboxylate;
each B is independently halo, hydroxy, carboxylate, carbamate ester or a carbonate ester;
Z of formula Ia is a substituted 5- or 6-membered, heterocyclic amine selected from the group consisting of pyrazole, imidazole and pyrazine, said heterocyclic amine having at least two alkyl substituents, wherein said alkyl substituent sterically hinders access of Pt atom to a DNA strand of a tumor cell, and wherein all substituents on the heterocycle are alkyl substituents;
Z of formula Ib is substituted 5- or 6-membered heterocyclic amine having at least two alkyl substituents, wherein said alkyl substituent sterically hinders access of the Pt atom to a DNA strand of a tumor cell, and wherein all substituents on the heterocycle are alkyl substituents;
and X is $NH_3$ or mono- or dialkyl substituted $NH_3$.

2. The complex of claim 1 wherein both A are halo.
3. The complex of claim 2 wherein both A are chloro.
4. The complex of claim 1 wherein both B are hydroxy or carboxylate.
5. The complex of claim 1 wherein X is $NH_3$.
6. The complex of claim 3 wherein X is $NH_3$.
7. The complex of claim 1 wherein Z is 1,3,5-trimethylpyrazole.
8. The complex of claim 1 wherein said at least one substituent is coupled to the heterocycle at a position other than the position adjacent to the coordinating atom in said heterocycle.
9. The complex of claim 1 wherein the solubility of the compound in aqueous solution is greater than or equal to 1 mg/ml.
10. A complex selected from the group consisting of
(SP-4-3)-amminedichloro(1,2-dimethylimidazole)platinum(II);
(SP-4-3)-amminedichloro(2,5-dimethylimidazole)platinum(II);
(SP-4-3)-amminedichloro(3,5-dimethylpyrazole)platinum(II);
(SP-4-3)-amminedichloro(1,3,5-trimethylpyrazole)platinum(II);
(SP-4-3)-amminedichloro(2,3-dimethylpyrazine)platinum(II);
(SP-4-3)-amminedichloro(2,5-dimethylpyrazine)platinum(II);
(SP-4-3)-amminedichloro(2,4,5-trimethyloxazole)platinum(II);
(SP-4-3)-amminedichloro(3,5-dimethylisoxazole)platinum(II);
(OC-6-43)-amminedichlorodihydroxo(1-dimethylimidazole)platinum(IV);

(OC-6-43)-amminedichlorodihydroxo(1,2-dimethylimidazole)platinum(IV);

(OC-6-43)-amminedichlorodihydroxo(2,5-dimethylimidazole)platinum(IV);

(OC-6-43)-amminedichlorodihydroxo(3,5-dimethylpyrazole)platinum(IV);

(OC-6-43)-amminedichlorodiacetato(2,3-dimethylpyrazine)platinum(IV); and (OC-6-43)-amminedichlorodihydroxo(2,3-dimethylpyrazine)platinum(IV).

11. A pharmaceutical composition comprising as active ingredient the complex of claim 1, in admixture with a pharmaceutically acceptable diluent or carrier and optionally one or more other therapeutic agents.

12. The composition of claim 11, in unit dosage form.

13. The composition of claim 11, for oral administration.

14. A cis-platinum complex of the formula Ia

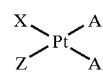

or a pharmaceutically acceptable salt thereof
wherein:
each A is independently halo, hydroxy or carboxylate;
each B is independently halo, hydroxy, carboxylate, carbamate ester or carbonate ester;
Z is a substituted 5- or 6Membered heterocyclic amine selected from the group consisting of pyrazole, imidazole oxazole and pyrazine, said heterocyclic amine having at least one alkyl substituent coupled to the heterocycle at a position one atom removed from the coordination atom in the heterocycle and wherein all substituents on the heterocycle are alkyl substituents;
and X is $NH_3$ or mono- or dialkyl substituted $NH_3$.

15. The complex of claim 14, wherein said complex is (SP-4-3)-amminedichloro(2-methylimidazole)platinum(II).

* * * * *